United States Patent
Simon

[11] Patent Number: 6,039,739
[45] Date of Patent: Mar. 21, 2000

[54] TARGETING APPARATUS FOR A LOCKING NAIL

[75] Inventor: Bernd Simon, Kiel, Germany

[73] Assignee: Howmedica GmbH, Germany

[21] Appl. No.: 09/287,895

[22] Filed: Apr. 7, 1999

[30] Foreign Application Priority Data

Apr. 9, 1998 [DE] Germany .................. 298 06 564 U

[51] Int. Cl.[7] ............................................. A61B 17/56
[52] U.S. Cl. ................................... 606/64; 606/62
[58] Field of Search .............................. 606/62, 104, 67, 606/64, 61, 60

[56] References Cited

U.S. PATENT DOCUMENTS

| | | | |
|---|---|---|---|
| 4,103,683 | 8/1978 | Neufeld | 606/64 |
| 4,913,137 | 4/1990 | Azer et al. | 606/64 |
| 5,281,224 | 1/1994 | Faccioli et al. | 606/62 |
| 5,354,300 | 10/1994 | Goble et al. | 606/80 |
| 5,928,235 | 7/1999 | Friedl | 606/64 |

*Primary Examiner*—Michael Buiz
*Assistant Examiner*—Tan-Uyen Ho
*Attorney, Agent, or Firm*—Lerner, David, Littenberg, Krumholz & Mentlik, LLP

[57] ABSTRACT

A targeting apparatus for a locking nail with a first section which is releasably connectable to the allocated end of the nail, with a bow-like second section connected to the first section, which comprises a receiving section running approximately parallel to the nail when the nail is connected to the first section and which comprises at least one transverse bore for the approximate fitting accommodation of a guiding sleeve. The receiving section consists of a first part rigidly formed with the second section and facing the first section, and of an outer second part movable relative to the first part against spring force, wherein the transverse bore extends through both parts and the bore in the parts is selected such that with a relaxed second part the sleeve is held in a slightly clamping manner and with a certain adjustment of the second part to the first part is freely displaceable in the bore.

14 Claims, 2 Drawing Sheets

TARGETING APPARATUS FOR A LOCKING NAIL

BACKGROUND OF THE INVENTION

The invention relates to a targeting apparatus for a locking nail.

Locking nails which may be introduced in the lower or upper femur mostly comprise transverse bores through which bone screws are guided in order to securely hold the locking nail in the bone channel. In particular by way of this a rotational securement is obtained.

A particular problem with locking nails is the location of the transverse bores with an implanted nail. For this therefore targeting apparatus are used. One category of targeting apparatus functions with X-rays. The transverse bores of the locking nail in the bone are imaged on a monitor. Further an imaging of the targeting element takes place. In this manner it is possible on the outer side to mark the location which lies on the axis of the transverse bores.

With another category, targeting apparatus are rigidly connected to one end of a nail. A bow-like section comprises at least one through-bore, whose axis is aligned to the axis of the transverse bore of the nail when it is mounted on the targeting apparatus. For guiding the drilling tool or the bone screw it is also known to insert a guiding sleeve through the transverse bore of the targeting apparatus, which is pushed forwards against the outer side of the bone.

Although the guiding sleeve sits fittingly in the transverse bore of the targeting apparatus, however by hand it must be able to be moved relatively easily in order not to make the work of the surgeon more difficult. By way of this however there exists the danger that with the handling of the targeting apparatus or on drilling and also on screwing in bone screws the guiding sleeve slides backwards.

BRIEF SUMMARY OF THE INVENTION

It is therefore the object of the invention to provide a targeting apparatus for a locking nail, with which the sleeve may be adjusted in a simple manner and may be fixed in the respective position.

With the targeting apparatus according to the invention the receiving section comprises two parts, wherein the one which faces the accommodated nail is rigidly connected to the remaining sections of the targeting apparatus, whilst the second part is movable relative to the first part against spring force. The transverse bore extends through both parts, wherein the part bores are arranged such that with a relaxed second part the sleeve is held in a slightly clamped manner. If in contrast the second part is pressed in the direction of the first part, the sleeve may be more or less freely displaced in the part bores.

If the sleeve is accommodated by the transverse bore of the targeting apparatus and pressed in the direction of the accommodated nail, this leads to a certain deformation of the second part in the direction of the first part, wherein the sleeve may be displaced against a certain resistance without an additional actuation being required. If here too large a force is to be exerted, a slight pressing on the second part is sufficient so that the sleeve may be displaced. With this the sleeve may also be displaced to the rear in the case that it is to be removed. It is essential however that the sleeve also with a relatively high force effort may not be retracted from the bore if the second part is not pressed in the direction of the first part. The pivotable second part with the attempt to retract the sleeve is pivoted away from the first part and increases the clamping effect. This increases with the exerted force, by which means the sleeve is securely held against sliding back.

There are various possibilities of realizing the design according to the invention. For this one formation envisages forming the first and a second part as one piece from elastic material. It is of course also conceivable to link the second part on the first and to let a spring act between both.

Another formation envisages the second part being attached to the free end of the first part and being separated from this by an approximately parallel slot.

The whole targeting apparatus may be formed as one piece, for example may be cast. It is however more advantageous to form the receiving section as one piece and the remaining apparatus as one piece since it is then more simple to select a suitable sufficiently resilient material for the receiving section. For the remaining sections on the other hand a relatively rigid and where appropriate stiff material is required, above all when the targeting apparatus at the same time is to be used as driving-in tool.

BRIEF DESCRIPTION OF THE DRAWINGS

The invention is hereinafter described in more detail by way of embodiment examples.

DETAILED DESCRIPTION OF THE INVENTION

Figure 1:
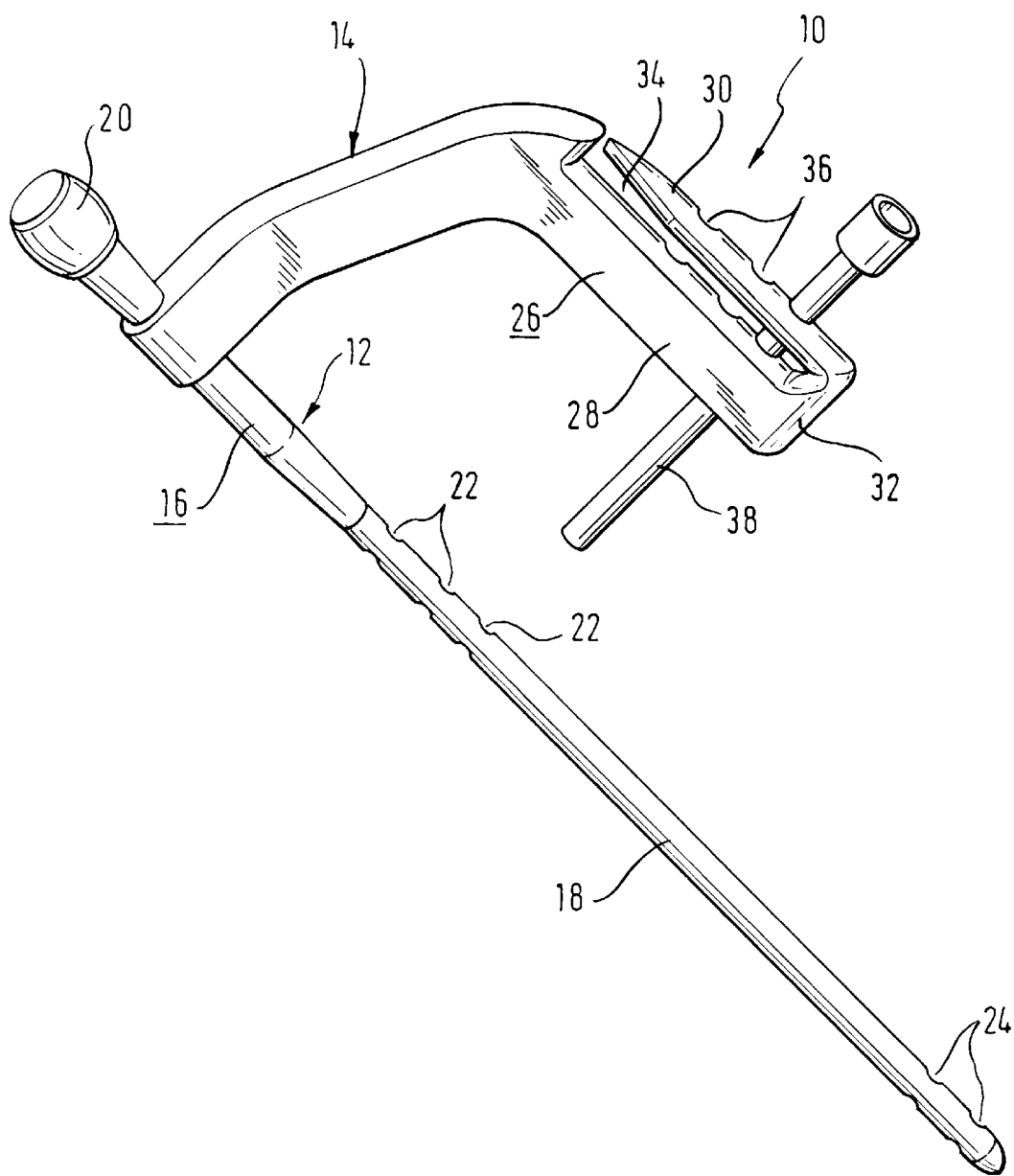
FIG. 1 shows perspectively a first embodiment form of a targeting apparatus according to the invention.

In FIG. 1 there is represented a targeting apparatus 10 which is composed of a first section 12 and a bow-like second section 14. The bow-like second section 14 on the left end comprises a through-bore for accommodating a fastening sleeve 16 which is rigidly fastened in this bore. The sleeve has at the lower end a connecting section (not shown) for connecting to a locking nail 18 known per se. Orientation means of the receiving section ensure that the nail 18 is connected to the sleeve 16 in a predetermined position. For this for example there serves a screw bolt, whose head 20 is to be recognized and whose thread cooperates with the inner thread section of the nail 18. The locking nail 18 comprises in the upper region at 22 transverse bores and in the lower region transverse bores 24. They serve for receiving bone screws (not shown) which are screwed transversely through the bone and through the transverse bores 22, 24, as is known per se.

The apparatus section 14 comprises a receiving section 26 which consists of a first part 28 and a second part 30. The first part is formed as one piece with the second section 14 and rigidly connected to this. The second part 30 is at the free end at 32 connected to the section 28 and is separated from this by an approximately parallel running incision 34. Since the material from which the section 14 is formed is resilient, the part 30 may be pivoted or bent to and away from this.

Transverse bores 36 extend through the parts 28, 30 and serve for accommodating a guiding sleeve 38 which is inserted through the lowest bore. The guiding sleeve 38 may in each case may be accommodated approximately fittingly by the bores 36 in the parts 28, 30, wherein however the position of the bores in the two parts 28, 30 is such that the sleeve in the relaxed position of the part 30 is held in a slightly clamped manner. If the part 30 is deformed slightly in the direction of part 28 the sleeve 38 may be easily displaced in the bores 36. If on the other hand the part 30 is deformed in the opposite direction, the sleeve 38 is clamped in and may no longer be moved.

The bores 36, in particular in the part 28, are aligned in their axis to the transverse bores 22. If a drilling tool is guided through the sleeve it drills the bone at a location which lies on the common axis of a transverse bore of the nail. For this procedure the sleeve 38 is displaced against the bone. A sliding back of the sleeve is prevented by the described clamping effect. If the sleeve however is to be removed, the part 30 is moved a little against the part 28.

Figure 2:
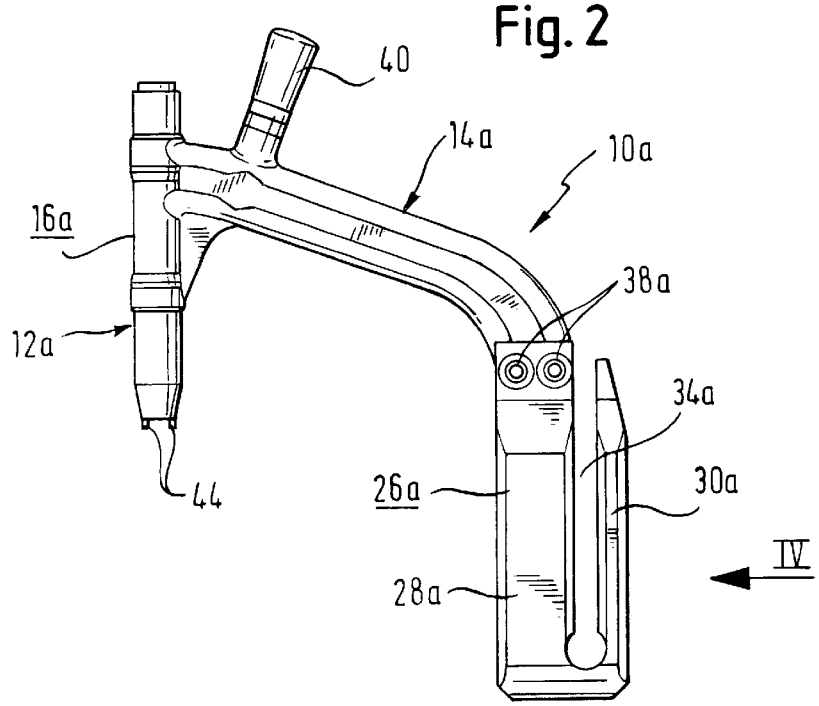
FIG. 2 shows a lateral view of a second embodiment form of a targeting apparatus according to the invention.
Figure 3:
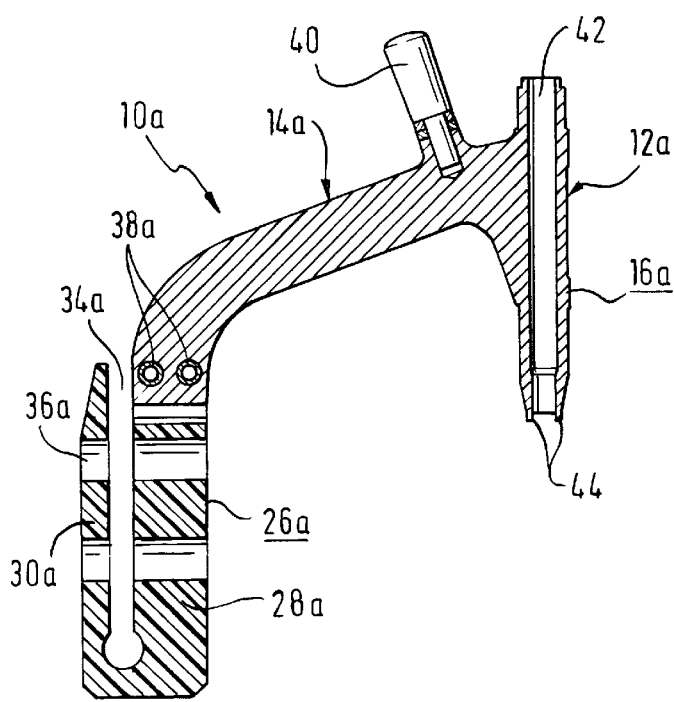
FIG. 3 shows a section through the targeting apparatus according to FIG. 2.
Figure 4:
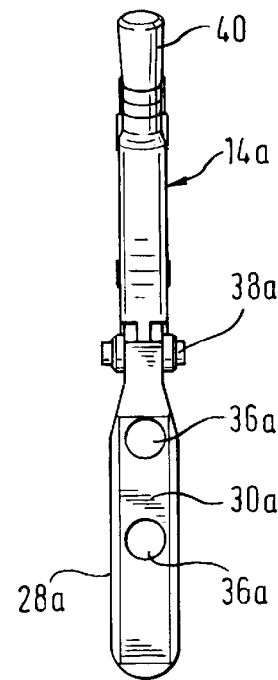
FIG. 4 shows a lateral view of the targeting apparatus according to FIG. 2 in the direction of arrow 4.

In the FIGS. 2 to 4 there is represented a targeting apparatus 10a which is similarly constructed to that according to FIG. 1. Therefore the same parts are provided with the same reference numerals, to which however an a is added.

One recognizes that with this embodiment form the receiving section 26a via connecting sleeves 38a is connected to the second section 14a. The section 14a is formed as one piece with the section 12a from a suitable metallic material, whilst for example the receiving section 26a consists of plastic material. Otherwise the receiving section 26a is formed completely equally to that according to FIG. 1.

One recognizes that the second section 14a comprises an upwardly standing hitting spike 40 which is fastened in a suitable manner. One recognizes in FIG. 3 that the first section 12a comprises a continuous bore 42 for receiving a fastening or screw bolt for mounting a locking nail. Two projections 44 at the lower end of the sleeve section 16a cooperate with non-shown recesses of a locking nail in order to give this the correct orientation.

The releasable fastening of the receiving section 26a has the advantage that various receiving sections may be attached according to the applied locking nail. If for example with regard to the bores 24 of the locking nail according to FIG. 1 a hole must be drilled into the bone, it requires another targeting apparatus. With the embodiment form according to FIGS. 2 to 4 therefore a fitting receiving section 26a may be attached to the remaining part of the targeting apparatus.

I claim:

1. A targeting apparatus for a locking nail with a first section which is releasably connectable to the allocated end of the nail, with a bow-like second section connected to the first section, which comprises a receiving section running approximately parallel to the nail when the nail is connected to the first section and which comprises at least one transverse bore for the approximate fitting accommodation of a guiding sleeve, wherein the receiving section consists of a first part rigidly formed with the second section and facing the first section, and of an outer second part movable relative to the first part against spring force, wherein the transverse bore extends through both parts and the bore in the parts is selected such that with a relaxed second part the sleeve is held in a slightly clamping manner and with a certain adjustment of the second part towards the first part is freely displaceable in the bore.

2. A targeting apparatus according to claim 1, wherein the first and second part are formed as one piece from an elastic material.

3. A targeting apparatus according to claim 2, wherein the second part is attached on the free end of the first part and is separated from this by a parallel slot.

4. A targeting apparatus according to claim 1, wherein the receiving section is formed as one piece.

5. A targeting apparatus according to claim 1, wherein the first and second section are formed as one piece.

6. A targeting apparatus according to claim 1, wherein the first part of the receiving section is connected to the second section via connecting elements.

7. A targeting apparatus according to claim 6, wherein the first and second part are formed from a suitable plastic material and the first section and the remaining second section are formed of metal.

8. A targeting device for use with a bone nail having at least one transverse bore for receiving a screw comprising:

a first portion connectable to a proximal end of said bone nail;

a second portion connected to said first portion having a first part and a second part moveable with respect to said first part, said parts each having at least one through bore for alignment with the at least one transverse bore in the bone nail; and a tubular guide for receiving the screw for insertion through the bores in said first and second parts, said first and second parts moveable with respect to one another to selectively clamp or release said tubular guide.

9. The targeting device as set forth in claim 8 wherein said first part and said second part are pivotally connected.

10. The targeting devise of claim 9 wherein said first and second parts are resiliently connected.

11. The targeting device as set forth in claim 8 wherein said second portion is made of an elastic material and has a generally U-shape with said first part forming a first leg of said U and said second part, forming the second leg of said U, said first and second legs bendable toward and away from one another to perform said selective clamping and release of said tubular guide.

12. The targeting device as set forth in claim 8 wherein said first and second parts have a plurality of through bores alignable with a plurality of through bores in said nail.

13. The targeting device of claim 8 wherein said first portion and said second portion are removably coupled to permit second portions having different size bores to be coupled to be coupled to said first portion.

14. A targeting device kit for use with bone nails having at least one transverse bore for a screw comprising:

a series of first portions connectable to a proximal end of said bone nails;

a series of second portions connectable to said first portions each second portion having a first part and a second part moveable with respect to said first part, said parts each having at least one through bore for alignment with the at least one transverse bore in the bone nail; and a tubular guide for receiving the screw for insertion through the bores in said first and second parts, said first and second parts moveable with respect to one another to selectively clamp and reduce said tubular guide.

* * * * *